United States Patent [19]

Cuntze et al.

[11] 4,312,631
[45] Jan. 26, 1982

[54] SURFACE-ACTIVE COMPOUNDS BASED ON NATURAL ROSIN ACIDS

[75] Inventors: Ulrich Cuntze, Charlotte, N.C.; Heinz Uhrig, Steinbach, Fed. Rep. of Germany

[73] Assignee: Hoechst Aktiengesellschaft, Frankfurt am Main, Fed. Rep. of Germany

[21] Appl. No.: 75,033

[22] Filed: Sep. 13, 1979

[30] Foreign Application Priority Data

Sep. 15, 1978 [DE] Fed. Rep. of Germany ....... 2840113

[51] Int. Cl.$^3$ .................. D06P 1/46; D06P 1/653; C09F 1/04; B01F 3/12
[52] U.S. Cl. .......................................... 8/583; 252/8.6; 252/8.7; 252/8.9; 252/354; 260/97; 260/98; 8/115.5; 8/115.7; 8/582; 260/104; 424/315; 8/116 R
[58] Field of Search ................. 252/354, 8.6, 8.7, 8.9; 260/98, 104, 97; 424/315; 8/92, 115.5, 116 R, 115.7

[56] References Cited

U.S. PATENT DOCUMENTS

| | | | |
|---|---|---|---|
| 2,178,830 | 11/1939 | Bruson | 260/98 |
| 2,184,770 | 12/1939 | Katzman | 252/356 |
| 2,679,529 | 5/1954 | De Groote | 252/354 |
| 2,950,272 | 8/1960 | Kirkpatrick | 260/104 |
| 3,408,174 | 10/1968 | Lindner | 252/354 |
| 3,594,123 | 7/1971 | Encke et al. | 23/165 |
| 3,671,461 | 6/1972 | Sheers et al. | 252/358 |

FOREIGN PATENT DOCUMENTS

| | | |
|---|---|---|
| 1769331 | 3/1972 | Fed. Rep. of Germany. |
| 946189 | 5/1949 | France. |
| 1008635 | 5/1952 | France. |

*Primary Examiner*—H. S. Cockeram
*Attorney, Agent, or Firm*—Curtis, Morris & Safford

[57] ABSTRACT

Compounds of the invention are obtained by oxyalkylating natural rosin acids, disproportionated rosin acids or rosin acids modified with aromatic hydroxy compounds or with cycloalkyl and especially aralkyl and aryl compounds capable of splitting off halogen, and the esterification products thereof with polyols, and furthermore by oxalkylating rosin alcohols, rosin maleinates and/or mixtures of the above-mentioned rosin substances with ethylene oxide and/or propylene oxide; reacting the alkylene oxide addition products thus obtained with maleic acid anhydride; and then adding alkali metal sulfite or alkaline earth metal sulfites or hydrogen sulfites to the maleic acid semiesters. These compounds are useful as interface-active agents, especially as dispersing agents for the fine division and stabilization of solids, and as wetting, emulsifying, levelling and dyeing auxiliaries.

22 Claims, No Drawings

SURFACE-ACTIVE COMPOUNDS BASED ON NATURAL ROSIN ACIDS

The present invention relates to interface active compounds on the basis of natural rosin acids.

Reaction products of rosin alcohols, rosin amines and rosin acids, and of the salts, anhydrides, esters, amides and halides thereof with polyglycol ethers or ethylene oxide, which contain per mol of the starting material at least one polyglycol chain having 8 or more ethylene oxide groups, are suitable for washing, wetting, cleansing, levelling and emulsifying and as anticorrosive agents (Ullmanns Encyklopädie der technischen Chemie, 3rd edition, volume 8, pages 408 et seq.).

Esterification products of rosin acids and rosin acid maleinates with polyalcohols, for example glycerol, pentaerythritol and sorbitol, are used—besides in the field of lacquers—in the preparation of printing inks and in the resining of paper sizes and as emulsifiers for the cold polymerization of butadiene-styrene mixtures in the preparation of caoutchouc (Ullmann, loc. cit., page 412, and J. Scheiber, Chemie und Technologie der künstlichen Harze (1943), page 560). Furthermore, for the preparation of dyes, lacquers and plastic materials there are used colophony-phenol compounds which are obtained by the addition of phenol, cresol or naphthol to natural rosin acids (German Pat. Nos. 581 956, 582 846, 652 602 and 536 170). German Pat. No. 689 392 relates to the preparation of tanning agents and textile auxiliaries by reactions of natural rosins, predominantly colophony, with aromatic hydroxy compounds in the presence of sulfuric acid as catalyst and condensation with formaldehyde and sodium sulfite.

The subject of the present invention is a compound of the formula $$A[(X-O)_x-Y-Z]_m$$

in which A stands for a resin radical, especially of a natural rosin acid, X stands for identical or different groups of the formulae $$-CH_2-CH_2- \text{ and } -CH_2-CH(CH_3)-,$$

Y represents identical or different radicals of the formula $$-C_nH_{2n}-$$

in which n is 2 or 3, and Z stands for identical or different radicals of the formulae $-OH$, $-O-CO-CH_2-CH(SO_3M)-COOM$, $-SO_3M$, $-O-SO_3M$, $-NR-CH_2-CH_2-SO_3M$, $-NR-(CH_2)_y-COOM$ or $-O-(CH_2)_y-COOM$ in which M represents a cation,
R is hydrogen or methyl, and
y is 1 or 2, at least one radical Z being different from $-OH$,
x is a number of from 1 to 100, and
m represents an integer of from 1 to 5.

The resin radical A is preferably derived from the following compounds:

(a) Natural rosin acids and/or their disproportionation products, as they are present in commercial types of colophony or are obtained therefrom, (b) rosin acid maleinates, as they are obtained from the rosin acids mentioned under (a) by reaction with maleic anhydride and subsequent esterification of the anhydride group, (c) rosin alcohols, as they are formed from the rosin acids mentioned under (a) by way of reduction, especially hydrogenation, (d) modified rosin acids, as they are obtained from the rosin acids mentioned under (a) by addition to, or condensation with, aromatic hydroxy compounds and/or aromatic intermediates capable of splitting off halogen (e) esterification products and/or their mixtures, as they are obtained by esterification from 1 mol of a di- to hexahydric, preferably low-molecular weight, alcohol with from 1 to 4, preferably 1 to 2 mols of a rosin acid and/or a modified rosin acid, as they are mentioned under (a) and (d).

Y is preferably $-CH_2-CH_2-$ or $$-CH_2-CH-;\\ \phantom{-CH_2-}CH_3$$

Z stands preferably for one of the following groups:

$$-O-CO-CH_2-CH-COOM,\\ \phantom{-O-CO-CH_2-CH-}SO_3M$$

$$-O-SO_3M, -SO_3M, -NH-C_2H_4-SO_3M,$$

$$-N-C_2H_4-SO_3M, -N-CH_2-COOM,\\ \phantom{-}CH_3 \phantom{-C_2H_4-SO_3M,-} CH_3$$

$$-O-(CH_2)_y-COOM \text{ or } -NH(CH_2)_y-COOM.$$

The index x is preferably 2 to 18, m is preferably 2 to 3 and M stands preferably for hydrogen, an alkali metal, one molar equivalent of an alkaline earth metal, or an ammonium group, especially an ammonium group deriving from a low-molecular alkylamine or alkylolamine.

Another subject of the invention is the use of these compounds as interface-active agents, especially as dispersing agents for the fine division and stabilization of solids, and as wetting, emulsifying, levelling and dyeing auxiliaries.

In the following, all percentages are by weight unless otherwise stated.

The compounds of the invention are obtained by oxalkylating natural rosin acids, disproportionated rosin acids or rosin acids modified with aromatic hydroxy compounds or with cycloalkyl and especially aralkyl and aryl compounds capable of splitting off halogen, and the esterification products thereof with polyols, and furthermore, by oxalkylating rosin alcohols, rosin maleinates and/or mixtures of the above-mentioned rosin substances with ethylene oxide and/or propylene oxide; reacting the alkylene oxide addition products thus obtained with maleic acid anhydride, amidosulfonic acid, chlorosulfonic acid or sulfur trioxide to give the corresponding semiesters; and then adding alkali metal sulfites or alkaline earth metal sulfites or hydrogensulfites to the maleic acid semiesters.

The condensation products, containing sulfo and carboxy groups, of the invention are obtained by adding one or several mol(s) of epichlorohydrin to the terminal hydroxy group(s) of the oxalkylates or by converting the terminal hydroxy group(s) into reactive groups, for example by halogenation, e.g. with thionyl chloride, and by reacting the halogen compounds thus obtained, for example, with sodium sulfite, or with isethionic acid, taurine, methyl taurine or suitable salts of these acids, such as sodium salts.

As starting materials there are suitable natural rosin acids, such as abietic acid, dehydroabietic acid, dihydroabietic acid, tetrahydroabietic acid, levopimaric acid, dextropimaric acid and isodextropimaric acid, as they are present in commercial types of colophony, as well as disproportionated, hydrogenated and dimerized rosin acids, rosin alcohols, such as abietyl alcohol and hydroabietyl alcohol (predominantly consisting of dehydroabietyl alcohol, dihydroabietyl alcohol and tetrahydroabietyl alcohol), and rosin maleinates, the anhydride group thereof having been esterified for example, with glycol, diglycol, glycerol, 1,1,1-trimethylolpropane, pentaerythritol or monohydric alcohols.

Further appropriate starting materials are rosinphenol compounds, as obtained by the addition of, for example, phenol, cresol, o-cresol acetate, salicyclic acid, guaiacol, bisphenol A, α- by β-naphthol, to natural rosin acids or commercial types of colophony in the presence of strongly acid catalysts or catalysts splitting off acid, such as boron trifluoride, hydrogen chloride, tin tetrachloride, aluminum chloride or strong mineral acids at a temperature of from 20° to 120° C. in an organic medium, in which process there is reacted from 0.5 to 0.8, preferably 0.7, mol of the above-mentioned phenols per 1 mol of rosin acid.

Furthermore, there are suitable modified natural rosin acids, as obtained by the reaction of natural rosin acids with araliphatic or aromatic compounds capable of splitting off halogen, for example, benzyl chloride, bis-(chloromethyl)-benzene, chloromethyl toluene, benzal chloride, chloromethyl naphthalene, 2-, 3- or 4-chlorophenol, 5-chloro-2-hydroxytoluene, 2-chloro-5-hydroxy-1,3-xylene, 4-chlorodiphenyl, 1- or 2-chloronaphthalene, 1-chloro-2-naphthol and 2-chloro-1-naphthol or with cycloaliphatic compounds, such as cyclohexyl chloride, in the presence of a catalyst, for example, 0.2% of zinc chloride, at a temperature of from 100° to 220° C., preferably from 150° to 210° C., in which process there is reacted per mol of rosin acid from 0.5 to 1.0, preferably 0.7 to 0.8, mol of the above-mentioned chlorinated hydrocarbons.

As representatives of the polyols for the esterification of the rosin acids there may be mentioned, for example: glycol, glycerol, 1,2,4-butane triol, butane diol-(1,4), 1,1,1-trimethylol propane, pentaerythritol, 2,4-dihydroxy-3-methylol pentane, hexane triol, sorbitol, anhydrosorbitol, hexitol or mannitol. The esterification of the rosin acids with the polyols is effected in a molar ratio of from 1:1 to 4:1, preferably from 1:1 to 2:1, in accordance with known esterification processes at a temperature of from 180° to 300° C., preferably from 200° to 270° C., optionally while adding an entrainer, such as an aromatic hydrocarbon or chlorinated hydrocarbon. As catalyst there may be used, for example, benzenesulfonic acid, p-toluene-sulfonic acid, boric acid, powdered tin or sulfuric acid.

The oxalkylation of the rosin acids, rosin acid maleinates, rosin alcohols and rosin acid esters is carried out according to known methods, preferably with an alkali metal hydroxide or alkali metal alkoxide as catalyst at a temperature of from 100° to 200° C., preferably from 140° to 170° C. The amount of alkylene oxide is proportioned such that, per carboxy group of the rosin acids and rosin acid maleinates and per hydroxy group of the rosin alcohols, there are added from 1 to 50, preferably from 2 to 18, mols, and per free hydroxy free of the rosin acid esters from 1 to 50 preferably from 3.5 to 9, mols of alkylene oxide. Suitable alkali metal hydroxides are potassium hydroxide and, preferably, sodium hydroxide, and as alkali metal alkoxides there may be used sodium methylate or ethylate; at the start of the oxalkylation the concentration should preferably be in the range of from 0.05 to 1.0%, calculated on rosin acid, rosin acid maleinate, rosin alcohol or rosin ester. The oxalkylation may be carried out without pressure or in pressure vessels with propylene oxide or preferably ethylene oxide, or mixtures of the same, the alkylene oxide optionally being fed in in a gaseous or liquid state. The working pressure is in the range of from 1 to 10, preferably from 2 to 8, bars.

In the following there are described in detail some suitable processes for the introduction of the anionic group(s).

The reaction of the oxalkylates with maleic anhydride to give the maleic acid semiesters is carried out by mixing the components and stirring at 20° to 100° C., preferably at 40° to 80° C., in the presence of alkali metal hydroxides, the concentration of which should be in the range of from 0.1 to 1.0%, calculated on the total mixture. Since maleic anhydride shows a tendency to sublimation, it is advantageous to operate in pressure vessels at an overpressure of from 0.2 to 1.0 bar of nitrogen or air and to ensure vigorous mixing, as the melted maleic anhydride is sparingly miscible with the oxalkylates at the beginning of the reaction. The amount of the maleic anhydride may be proportioned such that either all or only part of the terminal oxalkylate hydroxy groups or only part (but at least one) are reacted.

The conversion of these maleic acid semiester compounds into the corresponding sulfosuccinic acid semiesters is effected by addition of aqueous solutions of sulfites or hydrogensulfites. There are reacted for each maleic acid semiester group from 1.0 to 1.5, preferably from 1.05 to 1.1, molar equivalents of alkali metal or alkaline earth metal sulfite, alkali metal or alkaline earth metal hydrogensulfite or alkali metal or alkaline earth metal pyrosulfite. The sulfites are particularly appropriate, since in the case the di-salts of the sulfosuccinic acid semiesters are formed. The amount of water added may be in the range of from 50 to 85%, calculated on the total solution or mixture, and depends on the solubility of the sulfosuccinic acid semiester salts and on the viscosity of the solution. The reaction temperatures are in the range of from 20° to 100° C., preferably from 40° to 80° C.

The sulfation of the oxalkylates is carried out according to known processes. As sulfating reagent there may be used $SO_3$ gas, diluted with inert gas, or an $SO_3$ addition product, for example $SO_3$-dioxan, amidosulfonic acid or chlorosulfonic acid. There may be employed optionally an inert diluent, such as methylene chloride. The amount of the sulfating reagent to be used may be proportioned in a way that either all or only part of the terminal oxalkylate hydroxy groups or only part (but at least one terminal hydroxy group per molecule of the oxalkylate) are reacted. The sulfuric acid semiesters obtained in the form of the free acid in the sulfation with gaseous sulfur trioxide in inert gas may be converted into the desired salts by neutralization with the desired inorganic or organic bases.

For the preparation of the sulfo and carboxy group-containing condensation products, reactive groups, preferably chlorine atoms, are introduced into the molecule at the end of the ethylene oxide and/or ethylene oxide/propylene oxide chain(s). This is effected, for example, by the addition of epichlorohydrin to the terminal hydroxy group(s) in accordance with known processes at a temperature of from 20° to 100° C., preferably from 40° to 90° C., in the presence of tin tetrachloride, or by direct halogenation with halogenating agents, such as thionyl chloride, at a temperature of from 40° to 100° C., preferably from 40° to 80° C., in which process the terminal OH group(s) are exchanged totally or partially for chlorine atoms. The chlorine-containing intermediate thus obtained are reacted according to known processes with sodium sulfite in a pressure vessel at a temperature of from 100° to 200° C., preferably from 140° to 180° C., or with isethionic acid, methyl taurine, taurine or sarcosin at a temperature of from 40° to 60° C., in an alkaline medium at a pH of from 8 to 10.

The compounds of the invention and the mixtures thereof are clearly soluble in water and according to the Ross-Miles test (DIN 53 902) show only a minor tendency to foaming while lowering the surface tension according to the ring method for measuring the surface tension (DIN 53 914) up to an optimum of 30 $10^{-3}$ N/m. Besides, these compounds wet cotton fabric according to the dip-wetting method (DIN 63 901) within 30 to 240 seconds, are resistant to strong alkali as well as to strong acids under the common application conditions for surfactants and as detergents show an excellent anti-redeposition power. In the form of a spray-dried powder and as an aqueous solution the compounds of this invention show a very light color or are almost colorless, which avoids soiling effects in the dyeing of salt-forming fibers.

The compounds of the invention are excellently suitable as dispersing and wetting agents, for example for the preparation of highly pigmented and free flowing pigment preparations, preferably as dispersing agents for dyestuff dispersions, especially of disperse dyes, for the preparation of dispersions of optical brighteners, for the formulation of plant protective agents and pest control agents and as emulsifying agents for the preparation of carrier emulsions, especially of chlorobenzenes, chlorophenols, hydroxydiphenyls, diphenyl, phenyl phenols, aromatic carboxylic acid esters and alcohols as well as naphthalene and its derivatives, and as levelling and dyeing auxiliaries for the dyeing of natural and synthetic fiber material, such as cotton, wool, cellulose, spun rayon, cellulose acetate and triacetate, polyester, polyamide and polyacrylonitrile, or of fiber materials containing these substances.

The superiority of the substances of the invention to known anionic dispersing agents, such as lignin sulfonates or formaldehyde condensation products based on naphthalene-sulfonic acid, alkyl naphthalene-sulfonic acid and phenol-sulfonic acid as well as cresol formaldehyde or phenol formaldehyde and sodium sulfite, is to be seen in the fact that these substances show strong wetting properties in addition to markedly improved dispersing properties when applied in an aqueous medium. Furthermore, these substances are easily biodegradable.

The compounds of the invention may alternatively be employed in combination with non-ionic or other anionic compounds, builders and other additives and auxiliaries in dispersing and emulsifying formulations.

The following Examples serve to further illustrate the invention.

EXAMPLES

In the following Examples A to O the preparation of the compounds of the invention is described. The parts and percentages relate to the weight, and pressure values designate overpressure, unless otherwise stated.

Compound A (a) Preparation of the rosin acid oxalkylate

302 Parts of colophony are oxalkylated, after having added 2.2 parts of sodium methylate, in a pressure vessel, while stirring and by introducing 440 parts of ethylene oxide at 150° to 160° C., and maintaining a pressure of from 7 to 9 bars. After the total amount of ethylene oxide has been introduced under pressure, stirring is continued for 1 hour at a temperature of from 150° to 160° C. The rosin acid addition product obtained contains 10 mols of ethylene oxide.

(b) Preparation of the sulfosuccinic acid semiester

98 Parts of maleic anhydride are added, while stirring, to 742 parts of the above rosin acid oxalkylation product at 50° to 80° C.; after diluting the mixture with water, 132.3 to 138.6 parts of sodium sulfite (as an aqueous solution) are stirred in at 40° to 80° C. within 15 to 120 minutes, until the mixture has formed a clear solution. Subsequently, stirring is continued for 1 hour. The amount of water added may be in the range of from 50 to 85% by weight of the final solution.

Compound B (a) Preparation of the rosin alcohol oxalkylate

288 Parts of rosin alcohol (technical hydroabietyl alcohol of Messrs. Hercules) are oxalkylated, after having added 1 part of potassium hydroxide, in a pressure vessel, while stirring and feeding 364 parts of ethylene oxide at 150° to 160° C. and maintaining a pressure of from about 1.5 to 2 bars. After the total amount of ethylene oxide has been introduced under pressure, stirring is continued for 1 hour at 150° to 160° C. The rosin alcohol addition product obtained contains 8.3 mols of ethylene oxide.

(b) Preparation of the sulfosuccinic acid semiester

652 Parts of the above rosin alcohol oxalkylation product are esterified with 98 parts of maleic anhydride at 50° to 80° C., while stirring, and after diluting the mixture with water, from 132.3 to 138.6 parts of sodium sulfite (as an aqueous solution) are introduced by stirring at 40° to 80° C. within 15 to 120 minutes, until the mixture has become clearly water-soluble. Subsequently, stirring is continued for 1 hour. The amount of water added may be in the range of from 50 to 85% by weight of the final solution.

Compound C (a) Preparation of the rosin acid glycerol ester

302 Parts of disproportionated colophony are esterified, in the presence of 4 parts of powdered tin, with 92 parts of glycerol in a stirring vessel, while eliminating the reaction water by distillation, within 8 to 10 hours at 230° to 250° C., while simultaneously passing nitrogen through the vessel, until an acid number (AN) (DIN 53 183) of 25 has been reached.

(b) Preparation of the rosin acid glycerol ester oxalkylate

376 Parts of the above rosin acid glycerol ester are oxalkylated, after having added 2.7 parts of sodium methylate, in a pressure vessel, while stirring and feeding 308 parts of ethylene oxide at 150° to 160° C. and maintaining a pressure of from 2 to 8 bars. After the total amount of ethylene oxide has been introduced under pressure, stirring is continued for 1 hour at 150° to 160° C. The rosin acid glycerol ester addition product obtained contains 7 mols of ethylene oxide.

(c) Preparation of the di-sulfosuccinic acid semiester

690 Parts of the above rosin acid glycerol ester oxalkylate are esterified with 196 parts of maleic anhydride, while stirring at 50° to 80° C.; after diluting the mixture with water, 264.6 to 277.2 parts of sodium sulfite (as an aqueous solution) are introduced by stirring at 40° to 80° C. within 15 to 120 minutes, until the mixture has become clearly water-soluble. Subsequently, stirring is continued for 1 hour. The amount of water added may be in the range of from 50 to 85% by weight of the final solution. By way of spray-drying, a white powder is obtained which has a low electrolyte content.

Compound D (a) Preparation of the oxethylated rosin acid glycerol ester

302 Parts of colophony are esterified in accordance with the method described in Example C (a) with 92 parts of glycerol and then oxalkylated with 792 parts of ethylene oxide according to Example C (b). The rosin acid ester addition product obtained contains 18 mols of ethylene oxide.

(b) Preparation of the di-sulfosuccinic acid semiester

1094 Parts of rosin acid glycerol ester oxalkylation product are reacted according to Example C (c) with 196 parts of maleic anhydride and with 264.6 to 277.2 parts of sodium sulfite. After the spray drying, a slightly voluminous white powder is obtained.

Compound E (a) Preparation of the rosin acid pentaerythritol ester

468 Parts of colophony are esterified in the presence of 6.7 parts of boric acid with 204 parts of pentaerythritol in accordance with Example C (a) up to an AN of 14.8.

(b) Preparation of the rosin acid ester oxalkylate

428 Parts of the above rosin acid pentaerythritol ester are reacted, after having added 3.1 parts of sodium methylate, according to Example C (b) with 308 parts of ethylene oxide. The rosin acid ester addition product obtained contains 7 mols of ethylene oxide.

(c) Preparation of the tri-sulfosuccinic acid semiester

736 Parts of the above rosin acid ester oxalkylate are reacted according to Example C (c) with 294 parts of maleic anhydride and 378 parts of sodium sulfite to give the tri-sulfosuccinic acid semiester. By way of spray drying, a white powder is obtained which is almost free from salts.

Compound F (a) Preparation of the di-rosin acid-mono-sorbitol ester

604 Parts of colophony are esterified in the presence of 8 parts of powdered tin with 182 parts of sorbitol according to Example C (a). AN: 18.7.

(b) Preparation of the rosin acid sorbitol oxalkylate

750 Parts of rosin acid sorbitol ester (a) are reacted, after having added 5.4 parts of sodium methylate according to Example C (b), with 660 parts of ethylene oxide. The rosin acid sorbitol addition product obtained contains 15 mols of ethylene oxide.

(c) Preparation of the di-sulfosuccinic acid semiester

705 Parts of the above rosin acid sorbitol ester oxalkylate are reacted according to Example C (c) with 98 parts of maleic anhydride and 132.3 to 138.6 parts of sodium sulfite to give the disulfosuccinic acid semiester.

Compound G (C) Preparation of the tri-sulfosuccinic acid semiester from F(b)

705 Parts of rosin acid sorbitol ester of Example F (b) are reacted with 147 parts of maleic anhydride and 198.5 to 207.9 parts of sodium sulfite to give the trisulfosuccinic acid semiester.

Compound H (a) Preparation of the rosin oxalkylate

486 Parts of colophony maleinate rosin (melting point according to the capillary method (DIN 53 181) 110° to 118° C.; density (20° C.) 1.11; AN 10–20; iodine color number (DIN 6162) <30) are reacted, after having added 1 part of sodium methylate, according to Example A (a) with 440 parts of ethylene oxide. The rosin addition product obtained contains 10 mols of ethylene oxide.

(b) Preparation of the sulfosuccinic acid semiester

926 Parts of the above rosin addition product are reacted according to Example A (b) with 98 parts of maleic anhydride and 132.3 to 138.6 parts of sodium sulfite to give the sulfosuccinic acid semiester.

Compound I (a) Preparation of the rosin acid oxalkylate

302 Parts of colophony are oxalkylated according to Example A (a), after having added 2.2 parts of sodium methylate, while introducing 440 parts of ethylene oxide. The rosin acid addition product obtained contains 10 mols of ethylene oxide.

(b) Preparation of the sulfuric acid semiester

742 Parts of the above rosin acid addition product are mixed with 101.8 to 106.7 parts of amidosulfonic acid and 6 parts of urea and are stirred for 7.5 hours at 122° to 125° C. under a nitrogen atmosphere, until a light yellow and very viscous reaction product has been formed. For the conversion of the so-obtained ammonium salt into the sodium salt, 600 parts of water and 1000 parts of sodium hydroxide solution (of 24% strength) are added to 843.8 to 848.7 parts of the ammonium salt formed, and the mixture is heated to 70° C., while stirring and introducing nitrogen, until the total amount of ammonia has been eliminated. The aqueous final product contains 26% of sodium salt.

Compound K (a) Preparation of the rosin-phenol compound

At 10° C., 173.8 parts of a 25% solution of boron trifluoride in phenol are added within 4 hours to a solution of 604 parts of colophony in 800 parts of tetrachloromethane, and stirring is continued for 14 hours at a temperature of from 15° to 18° C. After working-up there are obtained 630 parts of a clear rosin having an AN of about 114 and a melting point of about 105° C.

(b) Preparation of the rosin oxalkylate

367 Parts of the modified rosin prepared under (a) are oxethylated, after having added 1.5 parts of sodium hydroxide, in a pressure vessel, while stirring and feeding 378.4 parts of ethylene oxide at 150° to 170° C., while maintaining a pressure of from 1.5 to 2.5 bars. After the total amount of ethylene oxide has been introduced under pressure, stirring is continued for 1 hour at 150° to 160° C. The rosin oxalkylate obtained contains 8.6 mols of ethylene oxide.

(c) Preparation of the di-sulfosuccinic acid semiester 745.4 Parts of rosin addition product (b) are esterified with 196 parts of maleic anhydride, while stirring at 50° to 85° C.; after diluting the mixture with water, 264.6 to 277.2 parts of sodium sulfite (as an aqueous solution) are introduced by stirring within 15 to 120 minutes at 40° to 80° C., and stirring is continued for 1 hour, after the mixture has become clearly water-soluble. The amount of water added may be in the range of from 50 to 85% by weight of the final solution. By way of spray-drying, a light yellow powder is obtained which exhibits a low electrolyte content.

Compound L (a) Preparation of the rosin-cresol compound

At 10° C., 200 parts of a 25% solution of boron trifluoride in technical cresol are introduced within 4 hours into a solution of 604 parts of colophony in 800 parts of tetrachloromethane, and stirring is continued for 14 hours at 15° to 18° C. After working-up there are obtained 767 parts of a clear rosin having an AN of 117 and a melting point of from 105° to 110° C.

(b) Preparation of the rosin-cresol-glycerol ester

377 Parts of rosin-cresol compound (a) are esterified, in the presence of 5 parts of powdered tin, with 92 parts of glycerol in a stirring vessel, while distilling off the reaction water, at a temperature of from 230° to 250° C. within 8 to 10 hours, while simultaneously passing nitrogen through the vessel, until an AN of about 25 has been reached.

(c) Preparation of the rosin-cresol-glycerol ester oxalkylate

451 Parts of rosin-cresol-glycerol ester (b) are oxalkylated according to Example K (b) with 440 parts of ethylene oxide, after 3.3 parts of sodium methylate have been added. The rosin ester addition product obtained contains 10 mols of ethylene oxide.

(d) Preparation of the di-sulfosuccinic acid semiester

891 Parts of rosin glycerol ester addition product (c) are reacted according to Example K (c) with 196 parts of maleic anhydride and from 264.6 to 277.2 parts of sodium sulfite. By way of a subsequent spray-drying process, a light yellow powder is obtained which is almost free from electrolytes.

Compound M (a) Preparation of the rosin-benzyl-glycerol ester

302 Parts of colophony are mixed with 80 parts of benzyl chloride and slowly heated to 100° C., whereupon the development of hydrogen chloride starts. This development may be accelerated by the addition of 0.2 part of zinc chloride. As soon as the development of hydrogen chloride is slowing down, the temperature is increased to 200° C. and is maintained for 1 hour at 200° to 210° C., until the reaction product is practically free from halogen. After it has been cooled to about 100° C. and 30 parts of glycerol and 100 parts of xylene have been added, the product is heated to 240° to 250° C. and maintained for about 4 hours at this temperature. Upon eliminating the volatile substances, a clear rosin is obtained which has an AN of 30 and a softening point of from 120° to 125° C.

(b) 384 Parts of rosin-benzyl-glycerol ester (a) are oxethylated according to Example K (b) with 440 parts of ethylene oxide, after having added 2.8 parts of sodium methylate. The rosin glycerol addition product obtained contains 10 mols of ethylene oxide.

(c) Preparation of the di-sulfosuccinic acid semiester

824 Parts of rosin glycerol ester addition product (b) are reacted according to Example K (c) with 196 parts of maleic anhydride and from 264.6 to 277.2 parts of sodium sulfite. After drying in the spray drier, a light yellow powder is obtained which has a minor electrolyte content.

Compound N

110 Parts of the oxalkylate according to Example D (a) are reacted with 36 parts of thionyl chloride at 40° C. and stirred for 2 hours at 80° C. After eliminating the excess thionyl chloride, the crude product is dissolved in 2000 parts of water, then 21 parts of sodium sulfite are added, and the product is maintained for 10 hours at 160° C. After working-up and isolating the product, there are obtained after the drying at 80° C. in vacuo from 111 to 118 parts of sodium sulfonate of the corresponding rosin acid glycerol ester addition product.

Compound O

After having heated 109.3 parts of rosin acid oxalkylate according to Example D (a) to 90° C., 0.5 part of tin tetrachloride is added; thereafter, 11.0 parts of technical epichlorohydrin are added dropwise within 10 minutes. Stirring is then continued for 2 hours at 80° C. After elimination of the catalyst the crude product is reacted with 19 parts of sodium sulfite within 4 hours at 160° C. After working-up and drying the product in vacuo at 80° C. there is obtained a sodium sulfonate of about 100% strength corresponding to Example N.

TEST EXAMPLES

For the comparison of the dispersing properties of compounds A to O, there are employed the test processes and dyestuffs described in German Offenlegungsschrift No. 21 32 403 (U.S. Pat. No. 3,775,056).

In test processes 1 to 3, different soluble dyestuffs are precipitated in the presence of increasing amounts of the surfactant to be tested at three pH values, and the fine division effected by the respective surface-active substance is examined. The numbers given in the Table indicate the ratio of the dyestuff to the surfactant at which the dyestuff can be dispersed without residue (i.e. the smaller the number given, the higher the dispersing power). In test process 4 a disperse dyestuff of medium dispersibility is finely distributed in a 1 liter agitating mill; the grinding period required in hours has been specified in Table 1. The dispersion being formed in this process is stored at 50° C. and examined repeatedly.

The Table shows the period of time tested (in days) in which the dispersion has not yet degraded. As a measure of dyeing properties at 130° C., polyester was dyed in accordance with known processes. The results have been indicated in Table 1 by numbers 1 to 5. The numbers have the following meanings:

1—no tinctorial strength;
2—poor;
3—useful;
4—good;
5—very good.

In comparison with the dispersing properties of Table 1, Table 2 shows the surface-active properties according to the following DIN standards:

Wetting power: DIN 53 901;
foaming properties: DIN 53 902; and surface tension: DIN 53 914.

The foaming properties were judged by the following scale:
- 0—non-foaming;
- 1—slightly foaming;
- 2—slight to medium foaming power;
- 3—medium foaming power;
- 4—strongly foaming.

The results of the compounds A to O of the invention were compared with the results of the known dispersing agents X and Y. Dispersing agent X is a commercial condensation product of naphthalene-2-sulfonic acid with formaldehyde which has been neutralized with sodium carbonate (Bios Final Report 762, middle of page 70; edition of Hobard Publishing Company, Washington, DC, U.S.), whereas dispersing agent Y was prepared according to Fiat Final Report 1013 from cresol, 1-naphthol-6-sulfonic acid, sodium sulfite and formaldehyde.

pound C and 110 parts of water in an agitation bead mill for 4 hours, until a fine division has been reached. After having added 50 parts of water, a 20% dye paste is obtained with a very fine division which meets all requirements with regard to coloring, especially those involved in the dyeing of polyester, polyester/wool and polyester/spun rayon mixed fibers.

Similarly favorable results are obtained with compounds A, D, G, L and M as well as with mixtures of these substances with compounds B, F, H, I and K in the ratio of 9:1 to 1:9, preferably from 3:1 to 1:3.

EXAMPLE 2

50 parts of the disperse dyestuff 4-(2-chloro-4-nitrophenylazo)-3-methyl-N-ethyl-N-$\beta$-cyanoethylaniline are ground according to Example 1 with 40 parts of compound C and 110 parts of water for 3 hours, until a fine division has been reached. The dispersion obtained is adjusted to a dyestuff content of 30% by adding 10

TABLE 1

| Compound | Test process 1 (pH 2-5) | 2 (pH 7) | 3 (pH 9-13) | 4 Grinding time (h) | Storage stability in days | Polyester dyeing at 130° C. |
|---|---|---|---|---|---|---|
| X | >5 | 0.125 | 0.5 | 5 | <1 | 3-4 |
| Y | 1.5 | 0.125 | >2 | 4 | >42 | 4-5 |
| A | 1 | 0.125 | 0.5 | 1 | >21 | 4 |
| B | 0.5 | 0.125 | 0.5 | 1 | <1 | 5 |
| C | 1 | 0.125 | 1 | 1 | >42 | 5 |
| D | 1 | 0.125 | 0.5 | 1 | >42 | 5 |
| E | 1 | 0.125 | 0.5 | 1 | >21 | 5 |
| F | 1 | 0.125 | 1 | 1 | >42 | 5 |
| G | 1 | 0.125 | 1 | 1 | >42 | 5 |
| H | 1 | 0.125 | 1 | 1 | <1 | 5 |
| I | 1 | 0.125 | 1 | 3 | <1 | 5 |
| K | 0.5 | 0.065 | 0.5 | 1 | >42 | 4 |
| L | 0.5 | 0.065 | 0.5 | 1 | >42 | 5 |
| M | 1 | 0.125 | 0.5 | 1 | >42 | 5 |
| N | >2 | 0.4 | 0.5 | 6 | <1 | 3 |
| O | >2 | >0.4 | 0.5 | 5 | <1 | 3 |

TABLE 2

| Comp. | Wetting power (sec.) 20° C. | 70° C. | Foaming power C = 2 g/l | Surface tension ($10^{-3}$ N/m) C = 2 g/l | Iodine color number C = 2 g/l |
|---|---|---|---|---|---|
| X | — | — | 0 | 71.30 | 1 |
| Y | — | — | 2 | 58.50 | 50 |
| A | 310 | 54 | 0 | 43.80 | 1 |
| B | 189 | 65 | 1 | 39.68 | 1 |
| C | — | 199 | 0 | 39.50 | 1 |
| D | 443 | 150 | 0 | 42.80 | 1 |
| E | — | 226 | 0-1 | 46.20 | 1 |
| F | — | — | 1 | 41.60 | 1 |
| G | — | — | 1 | 33.60 | 1 |
| H | — | 238 | 0-1 | 45.00 | 1 |
| I | — | 120 | 1 | 39.00 | 1 |
| K | 272 | 57 | 1 | 41.88 | 1 |
| L | — | 260 | 1 | 47.48 | 1 |
| M | — | 200 | 0-1 | 44.80 | 1 |
| N | — | 160 | 1 | 43.66 | 2 |
| O | — | 57 | 1 | 41.82 | 1 |

EXAMPLES OF APPLICATION

Besides this general comparison of the dispersing and wetting properties, the following Examples are represented to illustrate the wide field of application of the substances of the invention.

EXAMPLE 1

50 Parts of the disperse dyestuff 2-methyl-3-ethoxycarbonyl-6-morpholino-10-oxopyrazolo-[2,3-b]benzo[d,e]-isoquinoline are ground with 40 parts of compound C and 110 parts of water in an agitation bead mill parts of a naphthalene-sulfonic acid-formaldehyde condensation product and a further amount of an extender and then dried in a spray drier to give a powder. The dyestuff powder meets all coloristic and dyeing requirements. The same results are obtained with compounds D, E, K, L and M.

EXAMPLE 3

88.1 Parts of the disperse dyestuff mentioned in Example 1 are ground with 26 parts of compound C, 44 parts of glycol and 43.4 parts of water in an agitation bead mill for 4 hours, until a fine division has been reached. The paste is adjusted with water to a dyestuff concentration of 40%. The high-percentage dye paste obtained is excellently suitable for the preparation of printing pastes for transfer prints due to its favorable flow properties and its stability.

EXAMPLE 4

72.7 Parts of the disperse dyestuff 2-(4-bromo-3-hydroxy-quinolyl)-1,3-indanedione are finely divided in accordance with Example 3 with 20.6 parts of compound C, 36.4 parts of glycol and 73.1 parts of water, and the content of dyestuff is adjusted to 35% by the addition of water. The dye paste obtained shows favorable flow properties and meets the requirements with regard to transfer prints.

EXAMPLE 5

60 parts of the pigment Pigment Yellow 12 (Colour Index No. 21090) are ground in a solution of 16.4 parts of compound D in 57.5 parts of water, while adding 600 parts of sili-quartzite beads (diameter of 1 to 2 mm) as grinding bodies, for 2 hours in a 1 liter laboratory bead mill. After having added 20 parts of glycol, the grinding bodies are filtered off with suction via a sieve, and a pourable pigment dispersion is obtained which has a pigment content of 40% by weight.

Similarly favorable results are obtained with compounds C, L and M.

EXAMPLE 6

160 Parts of the brightener described in Example 1 of German Pat. No. 1 444 014 are ground with 10 parts of compound L and 160 parts of water in a bead mill for 2 hours, until a fine division has been reached, and the resulting dispersion is diluted to a content of 20% of brightener. A stable non-settling fluid dispersion is obtained. The same results are obtained with compounds C, D, E and M.

EXAMPLE 7

100 Parts of the plant protective agent 2-carbomethoxy-amino-benzimidazole are ground in a 1 liter agitation bead mill with 10 parts of compound D, 4 parts of the sodium salt of a polymerized alkylsulfonic acid, 10 parts of a fatty alcohol addition product based on a block polymer of polypropyleneglycol onto which ethylene oxide has been added, and 76 parts of water for 2 hours, until a fine division has been reached. Upon separating the grinding bodies, a very stable dispersion is obtained which shows a good suspension power without any deposit.

EXAMPLE 8

73.9 Parts of methyl naphthalene are stirred into a homogeneous mixture with 49.3 parts of the 53% formulation according to Example A; the concentrate is made up to 1 liter with water. A finely dispersed carrier emulsion is obtained, which shows in its usual dilution of 1:10 an excellent stability and which may be used for a prolonged period of time.

We claim:

1. A compound of the formula $$A[(X-O)_x-Y-Z]_m$$

wherein

A is the radical of a rosin acid or of a derivative thereof capable of reacting with a low-molecular alkylene oxide, x is a number of from 1 to 100 and m is an integer of from 1 to 5, X, when x and m are 1, is $$-CH_2-CH_2- \text{ or } -CH_2-CH(CH_3)-,$$

and, when x or m or both are greater than 1, is $$-CH_2-CH_2- \text{ or } -CH_2-CH(CH_3)-$$

or different groups of the formulae $$-CH_2-CH_2- \text{ and } -CH_2-CH(CH_3)-,$$

Y, when m is 1, is $-C_nH_{2n}-$ and, when m is greater than 1, stands for the same or different groups of the formula $$-C_nH_{2n}-,$$

wherein n is 2 or 3,

Z, when m is 1, is $-O-CO-CH_2-CH(SO_3M)-COOM$, and when m is greater than 1, is $-O-CO-CH_2-CH(SO_3M)-COOM$ or different groups of the formulae $$-OH \text{ and } -O-CO-CH_2-CH(SO_3M)-COOM,$$

M being a cation, with the proviso that at least one Z is not $-OH$.

2. A compound as claimed in claim 1, wherein A is the radical of a natural rosin acid or of a disproportionation product thereof.

3. A compound as claimed in claim 1, wherein A is the radical of a rosin alcohol obtained by reduction from a natural rosin acid or a disproportionation product of a natural rosin acid.

4. A compound as claimed in claim 1, wherein A is the radical of a natural rosin acid or a disproportionation product of a natural rosin acid reacted with cyclohexyl chloride, benzyl chloride, bis-chloromethyl-benzene, chloromethyl toluene, chloromethyl naphthalene, benzal chloride, chlorobenzene, bromobenzene, chlorophenol, chloronaphthalene, phenol, methyl phenol, methoxy phenol, chloro-hydroxytoluene, carboxy phenol, chloro-hydroxyxylene, naphthol or chloronaphthol.

5. A compound as claimed in claim 1, wherein A is the radical of a natural rosin acid; hydroabietyl alcohol; disproportionated rosin acid esterified with glycerol; natural rosin acid esterified with glycerol, pentaerythrit or sorbit; natural rosin acid reacted with maleic anhydride; natural rosin acid reacted with phenol; natural rosin acid reacted with cresol and esterified with glycerol; or natural rosin acid reacted with benzyl chloride and esterified with glycerol.

6. A compound as claimed in claim 1, wherein X is $-CH_2-CH_2-$.

7. A compound as claimed in claim 1, wherein x is a number of from 2 to 18.

8. A compound as claimed in claim 1, wherein Y is —$CH_2$—$CH_2$— or —$CH_2$—$CH(CH_3)$—.

9. A compound as claimed in claim 1, wherein m is 2 or 3, the groups $(X-O)_x$—Y—Z being the same or different.

10. A compound as claimed in claim 5, wherein X is —$CH_2$—$CH_2$—, x is 7 to 18, Y is —$CH_2$—$CH_2$—, Z is —OH or —O—CO—$CH_2$—$CH(SO_3Na)$—COONa, and m is 2 or 3.

11. A compound as claimed in claim 1, wherein A is the radical of a reaction product of maleic anhydride with a natural rosin acid or a disproportionation product of a natural rosin acid, said reaction product being esterified with a low-molecular weight aliphatic mono-, di-, tri-, tetra-, penta- or hexahydric alcohol.

12. A compound as claimed in claim 1, wherein A is the radical of an ester of 1 mol of a di-, tri-, tetra-, penta- or hexahydric low-molecular weight aliphatic alcohol with 1 to 4 mols of a natural rosin acid or a disproportionation product of a natural rosin acid.

13. A compound as claimed in claim 1, wherein A is the radical of an ester of 1 mol of a di-, tri-, tetra-, penta- or hexahydric low-molecular weight aliphatic alcohol with 1 to 4 mols of a natural rosin acid or a disproportionation product of a natural rosin acid reacted with cyclohexyl chloride, benzyl chloride, bis-chloromethylbenzene, chloromethyl toluene, chloromethyl naphthalene, benzal chloride, chlorobenzene, bromobenzene, chlorophenol, chloronaphthalene, phenol, methyl phenol, methoxy phenol, chlorohydroxytoluene, carboxy phenol, chloro-hydroxy-xylene, naphthol or chloronaphthol.

14. A method, which comprises adding a compound as defined in claim 1 to an aqueous composition in an amount effective to disperse a solid or emulsify a liquid in said composition, or wet a solid with said composition.

15. A method as defined in claim 14, wherein the aqueous composition is a dyeing or optical brightening liquid.

16. A method for treating a textile, which comprises treating said textile with an aqueous composition containing an amount of a compound as defined in claim 26 sufficient to effect the treatment.

17. A dye composition, which comprises a dye and an amount of a compound as claimed in claim 1 sufficient to effect dispersion or wetting of the dye in an aqueous composition.

18. A composition which comprises a pigment, a water-insoluble dyestuff or an optical brightener, and an amount of a compound as defined in claim 1 sufficient to effect dispersion or wetting of the pigment, dyestuff or brightener.

19. A biocidal composition, which comprises a biocidal agent and an amount of a compound as defined in claim 1 sufficient to effect dispersion or wetting of said agent.

20. A textile adjuvant composition, which comprises a dyestuff and an amount of a compound as claimed in claim 1 sufficient to effect dyeing of a textile or the leveling of such dyeing.

21. A composition, which comprises a surfactant compound as defined in claim 1 and another surfactant, said compound being present in an amount sufficient to effect dispersing or emulsifying capability of the composition.

22. A compound of the formula $$A[(X-O)_x-Y-Z]_m$$

wherein
A is the radical of a rosin acid or of a derivative thereof capable of reacting with a low-molecular alkylene oxide,
x is a number of from 1 to 100 and
m is an integer of from 1 to 5,
X, when x and m are 1, is —$CH_2$—$CH_2$— or —$CH_2$—$CH(CH_3)$—, and, when x or m or both are greater than 1, is —$CH_2$—$CH_2$— or —$CH_2$—$CH(CH_3)$— or different groups of the formulae

—$CH_2$—$CH_2$— and —$CH_2$—$CH(CH_3)$—,

Y, when m is 1, is —$C_nH_{2n}$— and, when m is greater than 1, stands for the same or different groups of the formula —$C_nH_{2n}$—, wherein n is 2 or 3, and Z, is —O—CO—$CH_2$—$CH(SO_3M)$—COOM, M being a cation.

* * * * *